United States Patent [19]

Hogue

[11] Patent Number: 4,720,998
[45] Date of Patent: Jan. 26, 1988

[54] CRUDE OIL SAMPLING SYSTEM

[76] Inventor: James D. Hogue, P.O. Box 126, Sundown, Tex. 79372

[21] Appl. No.: 874,053

[22] Filed: Jun. 13, 1986

[51] Int. Cl.$^4$ .......................... G01N 9/12; G01N 9/36
[52] U.S. Cl. ..................................... 73/444; 73/61 R; 73/863.83; 366/140; 366/142
[58] Field of Search ................. 73/444, 445, 446, 452, 73/453, 863.83, 863.84, 61 R, 61.1 R; 137/91; 366/140, 142

[56] References Cited

U.S. PATENT DOCUMENTS

| | | |
|---|---|---|
| 65,078 | 5/1867 | Hart . |
| 266,460 | 10/1882 | Gnadinger, Jr. . |
| 756,702 | 4/1904 | Porter ................................. 73/444 |
| 1,249,565 | 12/1917 | Wagner . |
| 1,589,418 | 6/1926 | Woidich . |
| 1,937,755 | 12/1933 | Ginger et al. . |
| 2,039,534 | 5/1936 | Holmes ............................. 366/142 |
| 2,316,019 | 4/1943 | Reese . |
| 2,972,255 | 2/1961 | Rachlin ............................. 73/452 |
| 3,222,918 | 12/1965 | Kuntz et al. ...................... 73/453 |
| 3,460,395 | 8/1969 | Shaw ................................. 73/440 |
| 3,605,782 | 9/1971 | Hollis et al. ...................... 137/91 |
| 3,952,761 | 4/1976 | Friedland ......................... 137/91 |
| 4,338,817 | 7/1982 | Callahan .......................... 73/448 |
| 4,494,413 | 1/1985 | Bukkems et al. ............... 366/140 |

Primary Examiner—John Chapman
Attorney, Agent, or Firm—Marcus L. Bates

[57] ABSTRACT

A crude oil sampling system that obtains and stores a representative sample of crude oil as the oil flows from a stock tank into a sales line. As crude oil flows from the storage tank during a finite period of time, a much smaller flow is diverted to a closed sample vessel. Accordingly, small sequential samples of the crude flowing from the stock tank is removed so that a true sample is protected within the closed vessel. Hence, the crude contained downstream of the stock tank changes in composition over a period of time while the crude contained within the sample vessel remains unchanged. When it is desired to evaluate the quality of the sample contained within the closed vessel, a circulation pump is energized and the contents of the sample vessel is thoroughly mixed. A hydrometer, including a thermometer associated therewith, is placed within a special gravity sample chamber which heretofore has been isolated from the sample vessel. Valves are opened to admit the homogenous sample into the gravity chamber, whereupon the hydrometer is read through a transparent wall of the gravity chamber. A sample is also withdrawn from the homogenous mixture and tested for sediments and water. The entire apparatus is easily cleaned and made ready to commence accumulating the next crude oil sample.

9 Claims, 7 Drawing Figures

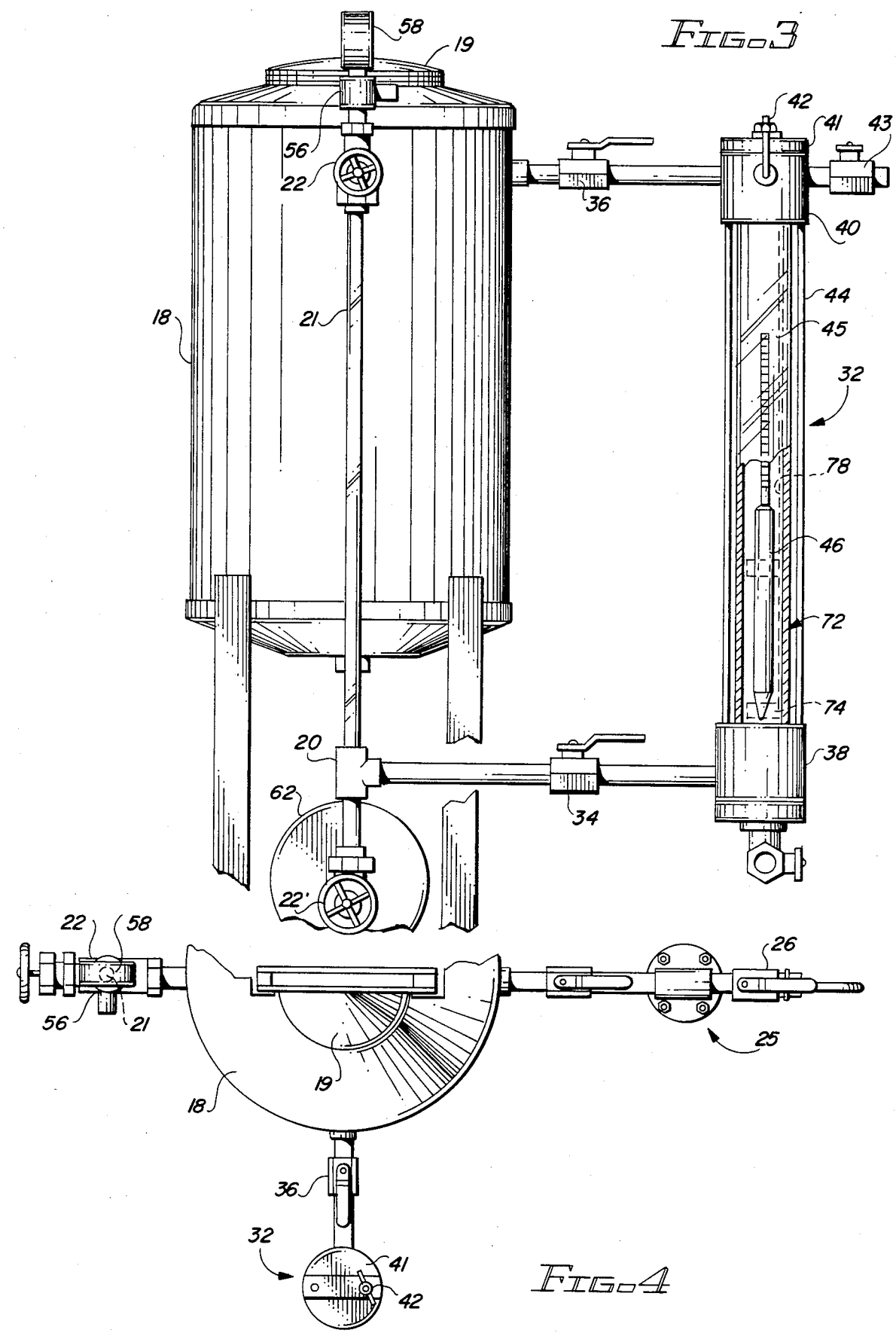

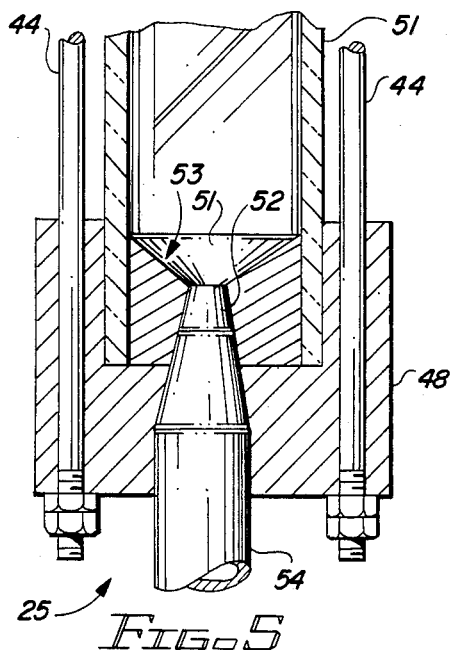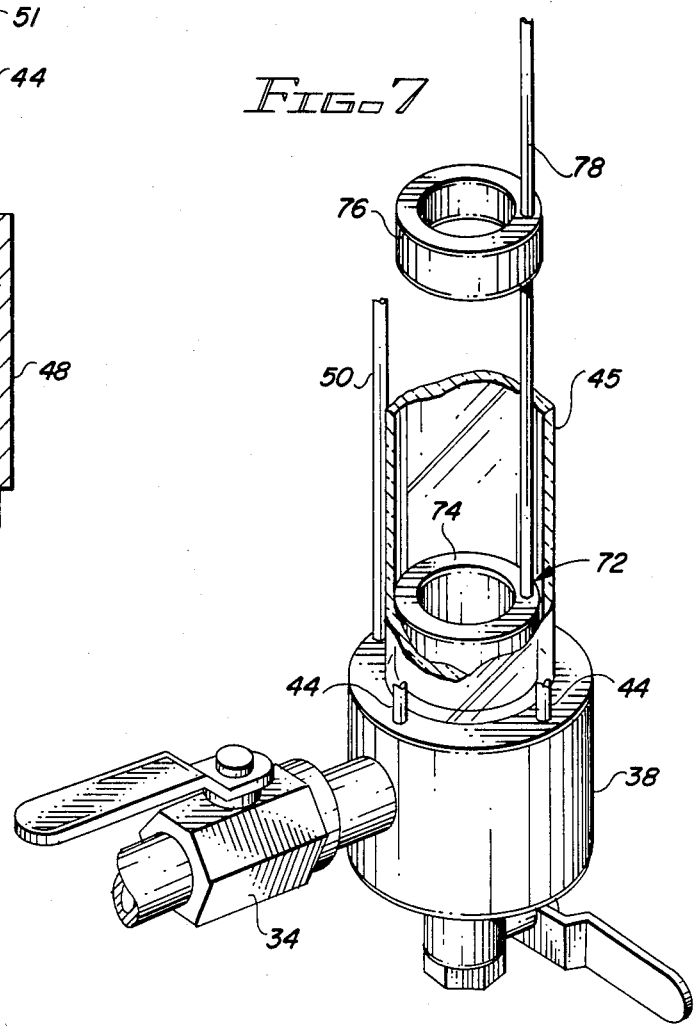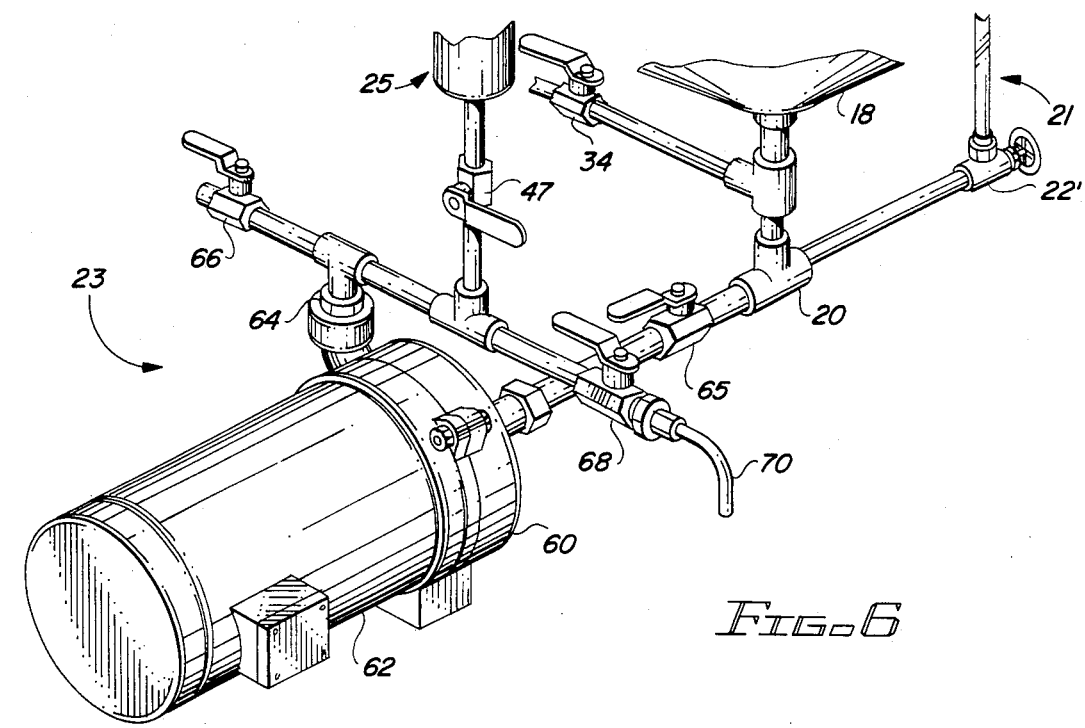

CRUDE OIL SAMPLING SYSTEM

BACKGROUND OF THE INVENTION

Crude oil produced from an oil well usually is pumped into a large storage tank holding hundreds of barrels of oil, and then the crude is continuously pumped from the storage tank and metered into a sales line. A small sample of the crude is removed from the flow line located downstream of the storage tank and the sample subsequently is used to determine the quality of the crude. This removed sample determines the price to be paid for the crude. The exact amount of money received for the crude oil is determined by gravity, sediment and water content. For example, fifteen cents per barrel is deducted for each one degree API increment below four degrees API for sour crude. Therefore, 0.4° API gravity increase would increase the price of the oil transferred to sales by six cents per barrel. This represents a lot of money when it comes to crude oil sales.

Oil stored in a vessel loses quality because the light ends cook off or escape into the atmosphere, also called weathering. Moreover, there is dirt, water, and other materials that gravitate toward the bottom of the storage tank that must be accounted for. Heretofore, it has not been possible to obtain a true representative sample of the hydrocarbons from crude that has accumulated in a sample vessel for many days.

Accordingly, it would be desirable to sequentially eject a finite quantity of produced crude flowing from a storage tank. These increments of oil accumulate concurrently with the flow of the crude from the storage tank, and therefore, the crude contained within the sample vessel is protected and is truly representative of the flow from the storage tank.

The method presently used to try to obtain a representative production sample is carried out on the contents of a small sample container. The gauger circulates the entire sample in the pot in order to place as much of the water and sludge contained in the bottom of the storage pot into suspension as is possible. The first substance to go through the circulation pump is water which is circulated back on top of the sample. The industry recommends that this circulation procedure continue for fifteen minutes, which is not always adhered to. Next, a 50cc sample is obtained downstream of the pump, and the sample is heated and then centrifuged to obtain the percent composition of the water and sediments. A reduction of the months volume of sales is based on this crude test.

Next, approximately one quart sample is removed from the pot which is subjected to an API gravity test. This sample is allowed to stand until all of the foam has broken out of the sample. The foamy action is caused by a sudden reduction of pressure which causes the hydrocarbon gases or light ends to escape into the atmosphere. These gases that escape into the atmosphere are light ends of hydrocarbons which have definite values in their relationship to the gravity of the oil.

These tests are carried out in order to arrive at the value of each months sales of the crude. It is apparent that these tests are inaccurate. The present invention insures that a true representative sample of the total months production is analyzed and that accurate gravity and S & W content can be ascertained.

S & W, as used herein, means sediment and water and once upon a time was called "BS & W".

PRIOR ART STATEMENT

U.S. Pat. No. 65,078 to Hart discloses an Indicator for Stills which shows externally the quantity, specific gravity, temperature, pressure, color, and rate of evaporation of the contents of the still. Note hydrometer K of the system. A sample of the fluid can be taken at 6, for example. This is an important reference.

U.S. Pat. No. 1,249,565 to Wagner discloses a Liquid Dispenser. Note the vertical glass tube 12 disposed on the exterior of tank 1 and by means of connections 13 and 14 is in communication with the interior of the tank. The tube 12 serves as a guideway for a common type of variable volume hydrometer 15 so that the purchaser may ascertain the exact grade of the gasoline or other liquid dispensed from the apparatus.

U.S. Pat. No. 1,937,755 to Ginger et al discloses an Apparatus For Examining Liquids. This apparatus is of special value and application in connection with the handling and storing of petroleum oils. By the use of this apparatus, the liquid in the refining system may be examined without removing the sample from the system. The loss of liquid, time, and instruments and danger of ignition attending customary practice are eliminated. The apparatus comprises a glass cylinder connected at the top and bottom through valves with the container whose contents are to be examined, and, except for a valve opening at the top, closed to the atmosphere, and an instrument for measuring the properties of the liquid is arranged within the cylinder.

U.S. Pat. No. 4,338,817 shows a hydrometer with temperature compensation, while U.S. Pat. No. 266,460 shows a try-box by which the proof of a liquid is determined.

U.S. Pat. No. 1,589,418 discloses the rate of flow, temperature, and gravity of a distillate.

U.S. Pat. Nos. 2,316,019 and 3,460,395 show fluid measuring devices. Friedman, U.S. Pat. No. 3,952,761 discloses a system for controlling the density of liquids in a processing system; and, Hollis et al, U.S. Pat. No. 3,605,782 shows a liquid mixing device having a pump, and a hydrometer positioned in a tank, wherein the hydrometer is connected to a control device.

SUMMARY OF THE INVENTION

This invention relates to a method of obtaining a representative sample of crude oil as the crude oil is being pumped to a sales facility. Small successive samples of the crude oil diverted from the sales flow line are pumped into a closed sample vessel thereby enabling a large sample to be accumulated over a finite period of time. The sample vessel is hermetically sealed from the atmosphere so that it remains a true representative sample of the flowing crude oil over a long period of time.

A hydrometer chamber is isolated from the sample vessel and can be directly connected thereto by valve means, thereby enabling the contents of the sample vessel to be transferred into the hydrometer chamber.

A suction or inlet of a pump is connected to receive the contents of the vessel, to flow the contents of the vessel through a mixing chamber, and back into the sample vessel, thereby intimately mixing the contents of the vessel and producing a homogeneous solution which flows in a circuitous pattern through the pump, mixing chamber, and vessel.

After the contents of the sample vessel have been mixed thoroughly, the hydrometer chamber is communicated with the contents of the vessel so that the representative sample is transferred from the vessel, into the hydrometer chamber, thereby enabling the specific gravity of the sample to be ascertained. At the same time, a small sample is removed from the vessel for determining the amount of sludge and water contained therein. This provides a means by which the quality of the representative sample can be determined.

The mixing chamber includes a jet nozzle connected to the pump outlet that directs a high velocity stream of the sample into a cavity of the mixing chamber. The mixing chamber includes a transparent wall so that the pumping and mixing action can be observed. This pumping and mixing action develops high shear forces between the different components of the sample and thereby provides a homogenized mixture wherein all of the hydrocarbons, water, and solids are uniformly distributed throughout the vessel sample.

A sight glass is connected to the vessel to enable the liquid level therein to be determined. Means are provided by which the vessel and attached parts can be thoroughly cleaned.

The present invention provides a method of evaluating the quality of produced crude oil by pumping successive small samples of the flowing crude into a closed sample vessel and thereby progressively accumulating a large isolated sample which is representative of the produced crude. This enables the true representative gravity of the crude, as it was produced or sold, to be obtained by mixing the large accumulated vessel sample until a homogenous mixture is achieved, and then measuring the specific gravity of the sample, and ascertaining the sludge and water content of the sample at the same time.

Accordingly, a primary object of the present invention is the provision of method and apparatus for subsequently evaluating the quality of flowing produced crude oil by accumulating a sample that is representative of the average condition of the crude as it is being produced or sold.

Another object of the present invention is the provision of a method of measuring the APT gravity of crude oil that has been accumulated within a sample vessel over a period of time.

A still further object of the present invention is the provision of method and apparatus for determining the quality of crude oil that has been sold from a stock tank, wherein the analysis is based on the condition of the crude as it originally flows from the storage tank.

An additional object of this invention is the provision of a system by which a mixture of liquids accumulated over a period of time within a sample vessel can be evaluated to determine the original quality of the mixture.

These and various other objects and advantages of the invention will become readily apparent-to those skilled in the art upon reading the following detailed description and claims and by referring to the accompanying drawings.

The above objects are attained in accordance with the present invention by the provision of a method for use with apparatus fabricated in a manner substantially as described in the above abstract and summary.

BRIEF DESCRIPTION OF THE DRAWINGS

FIG. 3 is a fragmentary, front elevational view of the apparatus disclosed in FIG. 2;

FIG. 4 is a fragmentary, top, plan view of part of the apparatus disclosed in FIGS. 2 and 3;

FIG. 5 is an enlarged, fragmentary, cross-sectional view of part of the apparatus disclosed in FIG. 2;

FIG. 6 is a fragmentary, perspective view of part of the apparatus disclosed in the foregoing figures; and, FIG. 7 is a fragmentary, perspective view of another part of the apparatus disclosed in the foregoing figures, with some parts being broken away therefrom and some of the remaining parts being shown in cross-section.

DETAILED DESCRIPTION OF THE PREFERRED EMBODIMENT

Figure 1:
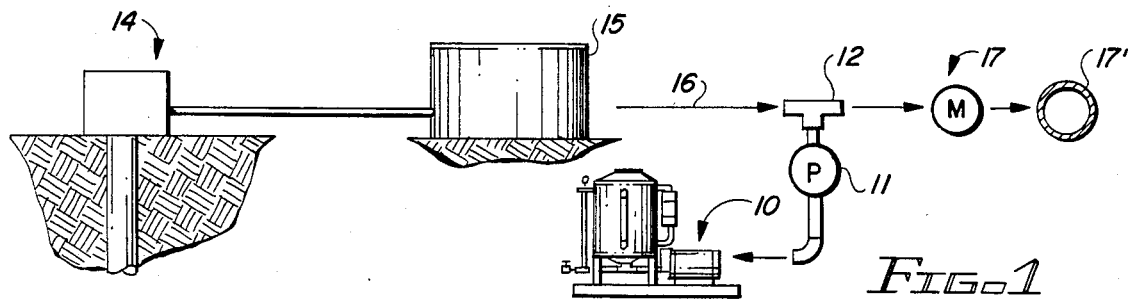
FIG. 1 is a flow sheet which diagrammatically shows the use of the present system.

FIG. 1 of the drawings discloses apparatus 10 for accumulating and subsequently determining the quality of crude oil. The apparatus 10 is connected to a sample regulator 11 which sequentially transfers a small sample from flow line 12 into the apparatus 10 at predetermined flow intervals.

An oil well 14 produces crude oil that is stored within a large storage tank 15. Flow line 16 continuously transfers the contents of stock tank 15 into a sales line 17'. For example, each barrel of oil metered at 17 signals regulator 11 to pump a 2 cc sample thereof into apparatus 10.

Figure 2:
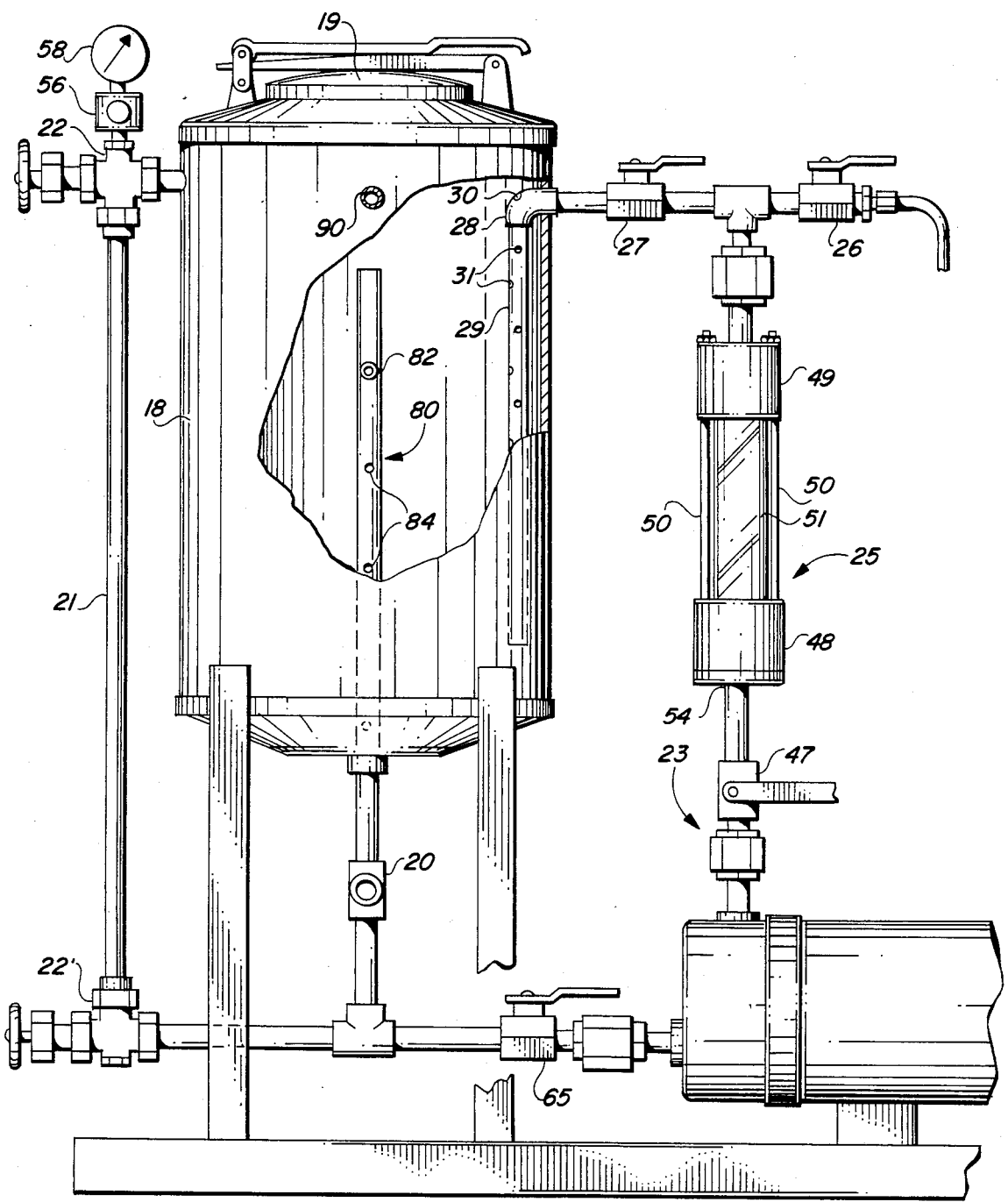
FIG. 2 is an enlarged, broken, part cross-sectional, side view of the present invention.

The apparatus 10, made in accordance with the present invention, is more fully disclosed in FIGS. 2-7. As seen in FIGS. 2 and 3, the apparatus 10 of this invention includes a hermetically sealed sample vessel 18 having a large diameter closure member that forms a clean-out hole 19 at the upper end thereof. An outlet tee 20 is located at the lower end of the vessel. Sightglass 21 is connected to the vessel by means of vertically spaced valves 22, 22'. The sightglass valves 22, 22' are known to those skilled in the art.

A circulating motor and pump assembly 23 is connected into the system for circulating the contents of the sealed sample vessel 18. The pump assembly 23 has an outlet thereof connected to flow back into the interior of the sample vessel 18 through the illustrated circuitous flow path that includes valve 47, mixing chamber 25, and valves 27 and 26. The flow from the pump 23 is directed through a modified elbow 28 to which an apertured downcomer 29 is connected. An outlet spray port 30 is directed towards the top of the vessel 18, while a series of apertures 31 are directed towards the sidewall of the interior of vessel 18.

As seen in FIGS. 3 and 4, together with other figures of the drawings, a gravity sample chamber 32 has an upper and a lower end thereof connected to the upper and lower ends of the vessel 18. Isolation valve 34 is connected to tee 20 while an upper isolation valve 36 is connected to the upper interior of the vessel 18. The gravity sample chamber 32 includes a lower header 38 and an upper header 40 spaced from one another. The header 40 includes a closure member in the form of an access door 41. A door latch 42 is provided by which the access door 41 sealingly engages the lower part of the header. Valve 43 connects the interior of the gravity sample chamber to ambient and is useful in cleaning the chamber.

Tie-rods 44 are connected between the lower and upper headers 38 and 40 and maintain a cylindrical glass chamber 45 in assembled relationship therewith.

A hydrometer 46 is telescopingly received through the apertured header 40 and is of a size to freely float within the chamber 32, when the chamber is properly filled with homogenized production fluid or crude oil. As seen in FIG. 3, the hydrometer 46 preferably includes a thermometer therewith so that the temperature and gravity of any liquid contained within chamber 32 can be accurately determined.

Looking again to the mixing chamber disclosed in FIGS. 2 and 5, and in particular to FIG. 2, it will be noted that a valve 47 is interposed between the mixing chamber 25 and the pump assembly 23. The mixing chamber includes a lower header 48 and an upper header 49, with there being tie-rods 50 which maintain a cylindrical glass chamber 51 secured in a sealed manner between the headers 48 and 49.

As best seen illustrated in FIG. 5, the mixing chamber 25 includes a nozzle 52 axially aligned with respect to the glass cylinder 51, with there being an annular area 53 formed between the chamber wall and the outlet of nozzle 52. Inlet pipe 54 is connected to the outlet of pump assembly 23, and thereby provides the flow velocity required to produce the shear forces between the components of the sample to thereby achieve a homogenized mixture, wherein each small drop of the mixture is a true representation of the entire sample contained within the sample vessel.

Still looking at FIG. 2, it will be noted that a popoff valve 56 is included in the system 10 so that should the pressure within chamber 18 exceed a preset value, a valve will be opened and thereby prevent the vessel from exceeding its designed structural limitations. Gauge 58 measures the pressure within vessel 18.

In FIG. 6, it will be noted that pump assembly 23 includes a centrifugal pump 60 driven by a suitable motor 62. The pump outlet 64 is connected to the before mentioned mixing chamber. Valve 65 is located between the tee 20 and the pump intake. Valves 66 and 68 permit a sample to be withdrawn from the sample vessel. Numeral 70 indicates a downwardly directed spout to facilitate rapidly obtaining a sample. Valve 66 permits the contents of vessel 18 to be emptied back into the sales line.

FIGS. 3 and 7 disclose a hydrometer holder 72 having a lower support member 74, a central support member 76, and a wire hanger 78. The hydrometer holder 72 bottom supports a hydrometer 46 at the lower end thereof and girdles the hydrometer at 76. The wire hanger 78 extends up into close proximity to and attaches to the cleanout door 41 of the upper header 40. The hydrometer holder enables the expensive and fragile hydrometer 46 to be easily telescopingly received within and removed from the sample chamber 32.

In FIG. 2, a vertical suction header 80 includes ports 82 and 84 formed therein through which the contents of the vessel 18 can flow toward pump assembly 23. The outlet ports become progressively smaller in a downwardly direction to enable equal flow of any stratified vessel contents therethrough.

The present invention provides an apparatus which is easily cleaned between each use thereof. The apparatus is cleaned by circulating an appropriate cleaning fluid through the pump assembly 23 and the mixing chamber 25. Thereafter, the cleanout manhole 19 can be removed so that the interior of the vessel 18 can be further cleaned.

In operation, after the apparatus 10 has been thoroughly cleaned, the valves 27, 34, 36 and 65 are closed and flow from the meter pump 11 can be commenced. The slow, intermediate, slugs of the production fluid flow into the inlet 90 and the sample fluid commences accumulating within the interior of the vessel. At this time, the valves 22, 22' to the sightglass 21 are in the open position while valves 34 and 36 are in the closed position. When the time arrives for evaluating the months sales, the representative sample of the fluid contained within the sample vessel is analyzed. This is achieved by opening valves 65, 47, 27 and starting the motor 62 so that pump 60 circulates the contents of vessel 18 through T 20, valve 65, pump 60, valve 47, mixing chamber 25, valve 27, and through the inlet ports formed in the downcomer 29.

The fluid flowing into the downcomer is sprayed through various apertures 30, 31 while the suction into the vertical suction header 80 receives fluid at various different elevations within vessel 18, and, accordingly, greatly aids in the mixing of the components of the sample contained within vessel 18. During the mixing process, the mixing chamber 25 can be viewed to make certain that ample mixing is occurring.

At this time closure member 41 is opened and lifted to gain access to the hydrometer carrier 72. The hydrometer 46 is placed within the carrier and carefully lowered into chamber 32, then closure member 41 is secured with latch member 42.

Valves 34 and 36 of FIG. 3 are closed during this time. The hydrometer 46 is carefully placed into operative configuration as illustrated in FIG. 3 by utilizing the hydrometer holder 72. Valves 34 and 36 are slowly moved to the opened position so that a representative thoroughly mixed sample is transferred into the hydrometer chamber 32. When the hydrometer has been in contact with the fluid long enough to reach equilibrium, the specific gravity and temperature is noted.

At the same time, a sample is taken at 70 for determining the amount of sludge and water present in the mixture contained within the vessel. This data provides an accurate analysis of the quality of the fluid flowed to the sales line.

The present invention provides method and apparatus by which a representative sample is accumulated which is equal to the original material pumped to a sales line. The present invention enables one to determine the historical flow composition of a flow line. The present method and apparatus enables fair play to be achieved in pricing crude oil that flows into a flow line.

I claim:

1. Method of evaluating the quality of a mixture of liquids flowing through a flow conduit over a long period of time comprising the steps of:

acumulating a large isolated sample of the liquid by pumping succesive small samples of the liquid into a closed sample vessel during said long period of time;

mixing the large isolated sample by connecting a centrifugal pump suction to a plurality of outlets located at different elevations within the interior of the sample vessel, and pumping the contents of the vessel through an outlet of a nozzle located within a mixing chamber, and flowing the mixture from the mixing chamber to a downcomer having a plurality of inlets located within said sample vessel;

forming an annular area about the nozzle discharge by providing an upwardly diverging cone about the end of the nozzle and thereby cause great turbulence to occur within the mixing chamber;

isolating a hydrometer within a transparent enclosure, connecting the enclosure to the sample vessel after the contents of the vessel having been thoroughly mixed so that the hydrometer is suspended in the mixed sample;

reading the hydrometer; and, withdrawing a sample from the mixed contents of the sample vessel so that the components of the mixture of liquids can be measured and identified.

2. The method of claim 1 wherein the hydrometer measures te specific gravity; and, the mixture of liquids is crude oil containing contaminants comprising water, dirt, and other debris.

3. The method of claim 1 and further including the steps of attaching a sightglass to the sample vessel to visually display the liquid level of the crude oil contained therewithin; and, forming a transparent sidewall in said mixing chamber through which the mixing process can be observed.

4. The method of claim 1 and further including the steps of hermeticaly sealing said hydrometer chamber until the contents of the vessel have been thoroughly mixed; providing an opening into said hydrometer chamber through which said hydrometer can be placed therein; and, supporting said hydrometer with a protective support device while placing the hydrometer within the hyrometer chamber.

5. A method for obtaining a crude oil sample from a flowing stream of produced crude oil which flows through a conduit comprising:

successively pumping a multitude of small samples from the flowing conduit into hermetically sealed sample vessel at predetermined intervals of time until the vessel is partially filled with the accumulated small samples;

obtaining a representative sample of the contents of the sample vessel by pumping the contents of the vessel from a plurality off outlets located at different elevations within the sample vessel, to the suction of a centrifugal pump, through a nozzle, into a mixing chamber, and to a downcomer having a plurality of inlets located within said vessel until a homogeneous mixture is obtained;

forming an annular area about the nozzle discharge by providing an upwardly diverging cone about the end of the nozzle and thereby cause great turbulence to occur within the mixing chamber;

flowing part of the homogeneous contents of the vessel into a hydrometer chamber which is separate from the vessel and connected thereto by a valve; measuring the sample specific gravity; and removing a sample of the homogeneous mixture and determining the amount of foreign matter contained therein.

6. The method of claim 5 and further including the steps of hermetically sealing said hydrometer chamber until the contents of the vessel have been thoroughly mixed; providing an opening into said hydrometer chamber through which said hydrometer can be placed therein;

supporting said hydrometer with a protective support device while placing the hydrometer within the hydrometer chamber, and then flowing part of the contents of the vessel into the hydrometer chamber.

7. Apparatus for obtaining a crude oil sample comprising a sample vessel within which the crude oil sample can be stored, means hermetically sealing said vessel, a cleanout hole in said vessel, a closure member of said cleanout hole, a sight glass for determining the liquid level in said vessel;

a jet mixing chamber; a hydrometer chamber for holding part of said crude oil sample; means by which a hydrometer can be placed within said hydrometer chamber; means connecting said hydrometer chamber to said sample vessel so that part of a sample can be transferred therebetween;

a centrifugal pump having a suction connected to receive the contents of said sample vessel; said pump having an outlet connected to said jet mixing chamber;

said jet mixing chamber including a nozzle having an outlet arranged in spaced relationship respective to the mixing chamber walls to provide an annulus between the chamber wall and the flow from the nozzle so that mixing can occur within the annulus; said mixing chamber walls upwardly diverge to form an upwardly diverging cone about the end of the nozzle and thereby cause great turbulence to occur within the mixing chamber;

said mixing chamber including an outlet connected to a downcomer located within said vessel, said downcomer having a plurality of inlet ports directed towards the interior sidewall of the vessel;

a vertical header positioned within said vessel, a plurality of outlet ports within said header, and means connecting said header to the suction of said centrifugal pump.

8. The apparatus of claim 7 and further including a valve connected to said vessel through which a homogeneous mixture of the contents of the vessel can flow while said pump is mixing the contents of the vessel to thereby enable a sample of the vessel contents to be withdrawn.

9. The apparatus of claim 7 and further including a valve by which the interior of said hydrometer chamber can be connected to said vessel to provide a homogeneous mixture of the contents of the vessel while said pump is mixing the contents of the vessel.

* * * * *